United States Patent
Patterson et al.

(10) Patent No.: US 10,576,307 B2
(45) Date of Patent: Mar. 3, 2020

(54) HAIR-TREATMENT COMPOSITIONS, METHODS, AND KITS FOR TREATING HAIR

(71) Applicant: L'OREAL, Paris (FR)

(72) Inventors: Kwana Patterson, Clark, NJ (US); Barbara Mitchell, Clark, NJ (US); Anand Mahadeshwar, Scotch Plains, NJ (US)

(73) Assignee: L'OREAL, Paris (FR)

( * ) Notice: Subject to any disclaimer, the term of this patent is extended or adjusted under 35 U.S.C. 154(b) by 164 days.

(21) Appl. No.: 15/604,189

(22) Filed: May 24, 2017

(65) Prior Publication Data

US 2018/0339175 A1 Nov. 29, 2018

(51) Int. Cl.
| | |
|---|---|
| *A61Q 5/12* | (2006.01) |
| *A61Q 5/00* | (2006.01) |
| *A61K 8/81* | (2006.01) |
| *A61K 8/362* | (2006.01) |
| *A61K 8/41* | (2006.01) |
| *A61K 8/58* | (2006.01) |
| *A61K 8/365* | (2006.01) |
| *A61K 8/36* | (2006.01) |
| *A61K 8/73* | (2006.01) |

(52) U.S. Cl.
CPC .................. *A61Q 5/12* (2013.01); *A61K 8/36* (2013.01); *A61K 8/362* (2013.01); *A61K 8/365* (2013.01); *A61K 8/41* (2013.01); *A61K 8/416* (2013.01); *A61K 8/585* (2013.01); *A61K 8/73* (2013.01); *A61K 8/81* (2013.01); *A61K 8/817* (2013.01); *A61Q 5/002* (2013.01); *A61K 2800/5426* (2013.01)

(58) Field of Classification Search
None
See application file for complete search history.

(56) References Cited

U.S. PATENT DOCUMENTS

| | | | | |
|---|---|---|---|---|
| 5,293,885 | A * | 3/1994 | Darkwa | A61K 8/447 132/203 |
| 5,951,969 | A | 9/1999 | Golinski et al. | |
| 5,985,803 | A | 11/1999 | Rizvi et al. | |
| 9,095,518 | B2 | 8/2015 | Pressly et al. | |
| 9,326,926 | B2 | 5/2016 | Pressly et al. | |
| 9,597,273 | B2 | 3/2017 | Pressly et al. | |
| 2007/0107142 | A1 | 5/2007 | Nguyen et al. | |
| 2011/0256084 | A1 * | 10/2011 | Dixon | A61K 8/042 424/70.2 |
| 2013/0149274 | A1 | 6/2013 | Nguyen et al. | |
| 2013/0251656 | A1 * | 9/2013 | Khenniche | A61K 8/58 424/70.13 |
| 2014/0171354 | A1 | 6/2014 | Miralles et al. | |
| 2015/0004117 | A1 | 1/2015 | Tan et al. | |
| 2015/0004119 | A1 | 1/2015 | Tan et al. | |
| 2015/0034119 | A1 | 2/2015 | Pressly et al. | |
| 2015/0037270 | A1 | 2/2015 | Pressly et al. | |
| 2015/0037271 | A1 | 2/2015 | Pressly et al. | |
| 2015/0290101 | A1 | 10/2015 | Pressly et al. | |
| 2015/0328102 | A1 | 11/2015 | Pressly et al. | |
| 2016/0175238 | A1 | 6/2016 | Shin et al. | |
| 2016/0235649 | A1 | 8/2016 | Streuli | |

FOREIGN PATENT DOCUMENTS

| | | |
|---|---|---|
| FR | 2966352 A1 | 4/2012 |
| JP | 63154611 A | 6/1988 |
| JP | 2015086211 A | 5/2015 |
| WO | WO-0152005 A1 | 7/2001 |
| WO | WO-2017/102855 A1 | 6/2017 |

OTHER PUBLICATIONS

Olaplex with relaxers, OLAPLEX™, pp. 1-2, Apr. 11, 2017, https://olaplex.es/olaplex-with-relaxers/.
Relaxers, Resource Library, Olaplex Education, pp. 1-2, Apr. 11, 2017, https://help.olaplex.com/detail/relaxers.
International Search Report and Written Opinion dated Nov. 16, 2018 for corresponding PCT Application No. PCT/US2018/034371.
Database GNPD: "Hydrating Hair Colour," 2017, pp. 1-6 www.gnpd.com.
Database GNPD: "Reconstructing Masque," 2012, pp. 1-6 www.gnpd.com.

* cited by examiner

*Primary Examiner* — Hasan S Ahmed
*Assistant Examiner* — Randeep Singh
(74) *Attorney, Agent, or Firm* — Polsinelli PC

(57) ABSTRACT

The instant disclosure relates to hair-treatment compositions that include a unique combination of components that function to impart desirable cosmetic properties to the hair, especially chemically treated hair. The hair-treatment compositions typically include: at least 0.5 wt. % of at least one non-polymeric mono, di, or tricarboxylic acid, and/or a salt thereof; one or more amines; one or more alkoxysilanes; one or more cationic polymers; and water. Hair treated with the hair-treatment compositions is strengthened and exhibits improved sensorial properties such as smoothness, softness, and suppleness.

11 Claims, No Drawings

HAIR-TREATMENT COMPOSITIONS, METHODS, AND KITS FOR TREATING HAIR

FIELD OF THE DISCLOSURE

The instant disclosure relates to hair-treatment compositions that are particularly useful for improving the quality of hair, especially chemically treated hair. The hair-treatment compositions strengthen the hair and improve the sensorial properties of the hair by imparting smoothness, softness, and suppleness. Also disclosed are kits that include the hair-treatment compositions and methods for using the hair-treatment compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades. The process of lifting the color of hair, also known as lightening (or bleaching), generally requires the use of oxidizing agents. Lightening of hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels can range from 1 (black) to 10 (light blond), one unit corresponding to one tone; thus, the higher the number, the lighter the shade or the greater the degree of lift.

In general, hair lightening or color lifting compositions and hair coloring or dyeing compositions possess an alkalinity such that these compositions have a pH value of above 7, typically being at pH 9 and above, and may generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effective alter the shape of the hair, these chemical treatments can damage the hair fibers and/or irritate the scalp. Thus, in order to reduce or avoid damage to hair, as well as to improve the cosmetic performance of the compositions, the use of new and additional components and novel combinations of ingredients are continuously sought.

However, the choice of components or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can chemically treat the hair while providing other cosmetic advantages such as shine, conditioning, fiber strength, and/or a healthy appearance to the hair, but avoiding or minimizing damage to the hair.

Further, both natural and sensitized or chemically treated hair can contain several kinds of negatively charged moieties, for example, carboxylates (resulting from the hydrolysis of amino acids and thioester bonds) and/or sulfonates (resulting from the oxidation of disulfide bonds). These negatively charged moieties can degrade the cosmetic properties of the hair. Moreover, when hair is chemically treated or damaged, the disulfide bonds in hair (disulfide linkages between two cysteine units) can be reduced or broken, resulting in the formation of thiol groups and/or cysteic acid.

SUMMARY OF THE DISCLOSURE

The instant disclosure relates to hair-treatment compositions that include a unique combination of components that function to impart desirable cosmetic properties to the hair, especially hair that has been chemically treated, for example with a chemical relaxer composition. For example, the hair-treatment compositions compensate for damage to hair or the loss of desirable cosmetic properties to hair that result from chemical treatments, including chemical relaxer treatments. After a chemical relaxer composition has been rinsed from the hair, the hair-treatment compositions of the instant disclosure can be applied to the hair alone or can be used with a shampoo and/or a conditioner (or another product) that is applied to the hair. Chemically relaxed hair treated with the hair-treatment compositions exhibit improved style-control, strength, discipline, frizz control, smoothness, and softness.

The hair-treatment compositions typically include:
- at least 0.5 wt. % of at least one non-polymeric mono, di, or tricarboxylic acid, and/or a salt thereof;
- one or more amines selected from the group consisting of diamines, polyamines, alkylamines, alkanolamines, and a mixture thereof;
- one or more alkoxysilanes;
- one or more cationic polymers; and
- water.

In some cases, one or more dicarboxylic acids and/or one or more tricarboxylic acids, and/or a salt thereof, are useful in the hair-treatment compositions. Non-limiting examples of dicarboxylic acid and/or a salt thereof, include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, and a salt thereof, and a mixture thereof. A particularly useful dicarboxylic acid and/or a salt thereof is malonic acid, and/or a salt thereof. Non-limiting examples of tricarbocylic acids, and/or a salt thereof, include citric acid, isocitric acid, aconitric acid, propane-1,2,3-tricarboxylic acid, benzene-1,3,5-tricarboxylic acid, and a thereof. A particularly useful tricarboxylic acid and/or a salt thereof is citric acid and/or a salt thereof.

With respect to the one or more amines, in some instances, the hair-treatment compositions include one or more alkylamines and/or alkanolamines. Non-limiting examples of alkanolamines include monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and a mixture thereof. Monoethanolamine is particularly useful in some cases.

Many alkoxysilane are known that may be used in the hair-treatment composition. Nonetheless, in some cases, particularly useful alkoxysilanes include aminoalkyltrialkoxysilanes, for example, 3-mercaptopropyltriethoxysilane and/or 3-aminopropyltriethoxysilane. Many useable cationic polymers are also known. Non-limiting examples of cationic polymers include poly(methacryloyloxyethyl trimethylammonium chloride), polyquaternium-37, quaternized cellulose derivatives, polyquaternium-4, polyquaternium-6, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof. In some cases, one or more poluquaterniums are useful, in particular, polyquaternium-6.

The hair-treatment compositions may be included in a kit. For example, a kit may include one or more hair-treatment compositions of the instant disclosure and one or more additional hair-treatment compositions, such as a shampoo and/or a conditioner. In some instances, the kit may include a hair-treatment composition of the instant disclosure, a shampoo, and a conditioner. Kits may also include a hair-treatment composition of the instant disclosure and a chemical relaxer composition. Such a kit may further include a shampoo and/or a conditioner. Typically, the various compositions of the kits are separately contained.

Finally, as mentioned previously, the hair-treatment compositions are unique in their ability to strengthen the hair and improve the sensorial properties of the hair by imparting smoothness, softness, and suppleness. Accordingly, the instant disclosure relates to methods for treating hair, for example, for improving the manageability of hair, for imparting lasting style and frizz control, for strengthening the hair, and for imparting smoothness and/or shine to the hair, etc.

DETAILED DESCRIPTION OF THE DISCLOSURE

The term "hair-treatment composition" encompasses many types of compositions for application to the hair, for example, chemical relaxer compositions, shampoos, conditioners, hair-rinses, hair lotions, hair gels, mouse-type products, sprays, etc. A hair-treatment composition is characterized by its ability to provide a cosmetic benefit to the hair. As is well-known, a shampoo provides cleansing benefits to the hair, a conditioner provides conditioning benefits to the hair, and gels can provide styling benefits to the hair. Non-limiting examples of additional benefits that can be imparted to hair include strength, smoothness, softness, and suppleness.

The hair-treatment compositions of the instant disclosure typically include:
  at least 0.5 wt. % of at least one non-polymeric mono, di, or tricarboxylic acid, and/or a salt thereof;
  one or more amines selected from the group consisting of diamines, polyamines, alkylamines, alkanolamines, and a mixture thereof;
  one or more alkoxysilanes;
  one or more cationic polymers; and
  water.

A non-polymeric mono, di, and/or tricarboxylic acid is an organic compound having one (mono), two (di), or three (tri) carboxylic acid groups (—COOH). The non-polymeric mono, di, and tricarboxylic adds, and/or salts thereof, typically have a molecular weight of less than about 500 g/mol, less than about 400 g/mol, or less than about 300 g/mol.

Non-limiting examples of monocarboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof. In some cases, the hair-treatment compositions include at least lactic acid and/or a salt thereof.

Non-limiting examples of dicarboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the hair-treatment compositions include oxalic acid, malonic acid, malic acid, maleic acid, a salt thereof, or a mixture thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair-treatment compositions include at least citric acid and/or a salt thereof.

In some cases, the hair-treatment compositions include at least one or more dicaboxylic acids, and/or a salt thereof, in particular, oxalic acid, malonic acid, malic acid, maleic acid, a salt thereof, or a mixture thereof. A particularly useful dicarboxylic acid is malonic acid and/or a salt thereof.

The total amount of the at least one non-polymeric mono, di, or tricarboxylic acid, and/or a salt thereof, is at least 0.5 wt. %, based on the total weight of the hair-treatment composition. In some cases, the total amount of the at least one non-polymeric mono, di, or tricarboxylic acid, and/or salt thereof, is at least 0.6, 0.7, 0.8, 0.9, or 1 wt. % up to about 15, 20, 25, or 30 wt. %. Furthermore, the total amount of the at least one non-polymeric mono, di, or tricarboxylic acid, and/or salt thereof, may be at least 0.5 wt. % to about 50 wt. %, at least 0.5 wt. % to about 40 wt. %, at least 0.5 wt. % to about 30 wt. %, at least 0.5 wt. % to about 20 wt.

%, at least 0.5 wt. % to about 10 wt. %, at least 0.5 wt. % to about 5 wt. %, at least 0.8 wt. % to about 50 wt. %, at least 0.8 wt. % to about 40 wt. %, at least 0.8 wt. % to about 30 wt. %, about 0.8 to about 20 wt. %, about 0.8 to about 10 wt. %, about 0.8 wt. % to about 5 wt. %, about 1 wt. % to about 50 wt. %, about wt. % to about 40 wt. %, about 1 wt. % to about 30 wt. %, about 1 wt. % to about 20 wt. %, about 1 wt. % to about 10 wt. %, about 1 wt. % to about 5 wt. %, about 2 wt. % to about 50 wt. %, about 2 wt. % to about 40 wt. %, about 2 wt. % to about 30 wt. %, about 2 wt. % to about 20 wt. %, about 2 wt. % to about 10 wt. %, or about 2 wt. % to about 5 wt. %.

Non-limiting examples of the types of amines that may be used in the hair-treatment compositions are vast, but may include diamines, polyamines, alkylamines, alkanolamines, and mixtures thereof. The one or more amines may be primary, secondary, tertiary amines, and mixtures thereof.

Non-limiting examples of diamines include ethylenediamine (1,2-diaminoethane), 1,3-diaminopropane (propane-1,3-diamine), putrescine (butane-1,4-diamine), cadaverine (pentane-1,5-diamine), hexamethylenediamine (hexane-1,6-diamine), 1,2-diaminopropane, diphenylethylenediamine, diaminocyclohexane, xylylenediamine (o-xylylenediamine, m-xylylenediamine, and p-xylylenediamine), phenylenediamine (o-phenylenediamine, m-phenylenediamine, p-phenylenediamine), 2,5-diaminotoluene, dimethyl-4-phenylenediamine, N,N'-di-2-butyl-1,4-phenylenediamine, 4,4'-diaminobiphenyl, 1,8-diaminonaphthalene, and mixtures thereof.

Polyamines have more than 2 amino groups and may be a polymer comprising multiple amino groups including homopolymers, copolymers, and terpolymers. For instance, the polyamine may be an alkoxylated polyamine having at least two amino groups and at least one degree of alkoxylation. The alkoxylation is provided by an alkylene oxide group such as, for example, ethylene oxide and/or propylene oxide. In some cases, the compositions do not include polymers having dimethylamino moieties, i.e., the compositions are free of essentially free of polyamines that are polymers having dimethylamino moieties.

Non-limiting examples of alkylamines and alkanolamines include compounds of formula (II):

$NR_3R_4R_5$ (II)

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some cases, $R_3$, $R_4$ and $R_5$ are independently H, $C_1$-$C_2$ alkyl, $C_1$-$C_{20}$ monohydroxyalkyl or $C_2$-$C_{20}$ polyhydroxyalkyl, provided that at least one of $R_3$, $R_4$ and $R_5$ is an alkyl or mono or polyhydroxyalkyl. Finally, $R_3$, $R_4$ and $R_5$ may independently be H, $C_1$-$C_{10}$ alkyl, $C_1$-$C_{10}$ monohydroxyalkyl or $C_2$-$C_{10}$ polyhydroxyalkyl, provided that at least one of $R_3$, $R_4$ and $R_5$ is an alkyl or mono or polyhydroxyalkyl.

Non-limiting examples of alkanolamines include monoethanolamine, diethanolamine, triethanolamine, monoisopropanolamine, diisopropanolamine, N-dimethyl-amino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

The total amount of the one or more amines may vary, but in some cases, the total amount of the one or more amines is about 0.1 to about 50 wt. %, based on the total weight of the hair-treatment composition. In some cases, the total amount of the one or more amines is about 0.1 to about 50 wt. %, about 0.1 to about 30 wt. %, about 0.1 to about 25 wt. %, about 0.1 to about 20 wt. %, about 0.1 to about 15 wt. %, about 0.1 to about 10 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, or about 3 to about 8 wt. %.

The hair-treatment compositions typically include one or more alkoxysilanes. Non-limiting examples include methyltrimethoxysilane, methyltriethoxysilane, glycidoxypropyltrimethoxysilane, vinyltrimethoxysilane methacryloxypropyltrimethoxysilane, methacryloxypropyltrimethoxysilane, acryloxypropyltrimethoxysilane, vinyltrimethoxysilane, glycidoxypropyltriethoxysilane, glycidoxypropyltrimethoxysilane, aminopropyltriethoxysilane, aminopropyltrimethoxysilane, mercaptopropyl-trimethoxysilane, mercaptopropyltriethoxysilane, and a mixture thereof. Additional non-limiting examples include vinyltrimethoxysilane, vinyltriethoxysilane, vinyltripropoxysilane, aryltrimethoxysilane, aryltriethoxysilane, N-(3-acryloxy-2-hydroxypropyl)-3-aminopropyltriethoxysilane, N-(3-acryloxy-2-hydroxypropyl)-3-aminopropyltrimethoxysilane, N-(3-acryloxy-2-hydroxypropyl)-3-aminopropyltripropoxysilane, 3-acryloxypropylmethylbis(trimethoxy)silane, 3-acryloxypropyltrimethoxysilane, 3-acryloxypropyltriethoxysilane, 3-acryloxypropyltripropoxysilane, 3-(meth)acryloxypropyltrimethoxysilane, 3-(meth)acryloxypropyltriethoxysilane, 3-(meth)acryloxypropyltripropoxysilane, styrylethyltrimethoxysilane and a mixture thereof. In some instances, particularly useful alkoxysilanes include 3-mercaptopropyltriethoxysilane and/or 3-aminopropyltriethoxysilane. A more exhaustive list of alkoxysilanes that may be included in the hair-treatment compositions is provided later, under the heading "Alkoxysilanes."

The total amount of the one or more alkoxysilanes may vary but is typically about 0.1 to about 20 wt. %, based on the total weight of the hair-treatment composition. The total amount of the one or more alkoxysilanes may be about 0.1 to about 15 wt. %, about 0.1 to about 10 wt. %, about 0.1 to about 8 wt. %, about 0.1 to about 6 wt. %, about 0.5 to about 20 wt. %, about 0.5 to about 15 wt. %, about 0.5 to about 10 wt. %, about 0.5 to about 8 wt. %, about 0.5 to about 6 wt. %, about 1 to about 20 wt. %, about 1 to about 15 wt. %, about 1 to about 10 wt. %, about 1 to about 8 wt. %, or about 1 to about 6 wt. %.

One or more cationic polymers are typically included in the hair-treatment compositions. Non-limiting examples of cationic polymers include poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof. In some cases, the hair-treatment compositions include one or more polyquaternium polymers, for example, polyquaternium-6. In some instances, the one or more cationic polymers are selected from the group consisting of polyquaternium-4, polyquaternium-6, polyquaternium-7, polyquaternium-22, paolyquaternium-36, and a mixture thereof. A more exhaustive list of cationic polymers that may be included in the hair-treatment compositions is provided later, under the heading "Cationic Polymers."

The total amount of the one or more cationic polymers may vary but is typically about 0.01 to about 10 wt. %, based on the total amount of the hair-treatment composition. The total amount of the one or more cationic polymers may be about 0.01 to about 8 wt. %, about 0.01 to about 6 wt. %, about 0.01 to about 4 wt. %, about 0.05 to about 10 wt. %, about 0.05 to about 8 wt. %, about 0.05 to about 6 wt. %, about 0.05 to about 4 wt. %, about 0.1 to about 10 wt. %, about 0.1 to about 8 wt. %, about 0.1 to about 6 wt. %, or about 0.1 to about 4 wt. %.

In one embodiment, the hair-treatment compositions of the instant case include:
- at least 0.5 to about 20 wt. %, about 1 to about 15 wt. %, or about 5 to about 15 wt. % of at least one non-polymeric mono, di, or tricarboxylic acid and/or a salt thereof, for example, one or more dicarboxylic acids and/or a salt thereof, selected from the group consisting of oxalic acid, malonic acid, malic acid, maleic acid, a salt thereof, or a mixture thereof (such as malonic acid and/or a salt thereof);
- about 1 to about 20 wt. %, about 1 to about 15 wt. %, or about 1 to about 10 wt. % of one or more alkanolamines, for example, one or more alkanoloamines, for example, one or more alkanolamines selected from the group consisting of monoethanolamine, 2-aminopropan-1-ol and 1-aminopropan-2-ol, 1,2,3-triaminopropane, 1,3-diaminopropan-2-ol, 1,2-diamino-propan-3-ol, 1-aminopropanediol, 2-aminopropanediol, glucosamine, isomaltine, and a mixture thereof;
- about 0.1 to about 20 wt. %, about 0.1 to about 15 wt. %, or about 0.1 to about 10 wt. % of one or more alkoxysilanes, for example, one or more alkoxysilanes selected from the group consisting of 3-mercaptopropyltriethoxysilane, 3-aminopropyltriethoxysilane, and a mixture thereof; and about 0.01 to about 10 wt. %, about 0.01 to about 8 wt. %, or about 0.1 to about 8 wt. % of one or more cationic polymers.

In another embodiment, the hair-treatment compositions of the instant case include:
- at least 0.5 to about 20 wt. %, about 1 to about 15 wt. %, or about 2 to about 15 wt. % of malonic acid, and/or a salt thereof;
- about 1 to about 20 wt. %, about 1 to about 15 wt. %, or about 1 to about 10 wt. % of monoethanolamine;
- about 0.1 to about 20 wt. %, about 0.1 to about 15 wt. %, or about 0.1 to about 10 wt. % of 3-mercaptopropyltriethoxysilane and/or 3-aminopropyltriethoxysilane; and
- about 0.01 to about 10 wt. %, about 0.01 to about 8 wt. %, or about 0.1 to about 6 wt. % of one or more cationic polymers selected from polyquaterniums, in particular, polyquaternium-6.

The hair-treatment compositions of the instant disclosure may be incorporated into a kit. For example, the kits may include at least one hair-treatment composition according to the instant disclosure (a hair-treatment composition comprising 0.5 wt. % of at least one non-polymeric mono, di, or tricarboxylic acid, and/or a salt thereof, one or more amines, one or more alkoxysilanes, one or more cationic polymers, and water) and one or more additional hair-treatment compositions, for example, a hair relaxer composition, a shampoo, a conditioner, etc. The various hair-treatment compositions are separately contained in the kits. In some instances, the kits include one or more hair-treatment compositions (according the instant disclosure), a shampoo, and/or a conditioner, all of which are separately contained. The kits may also include one or more hair-treatment compositions (according the instant disclosure), a chemical relaxer composition, and optionally a shampoo and/or a conditioner. Instructions, mixing components, brushes, gloves, measuring tools, etc., may also be included in the kits.

A non-limiting example of kit includes: (A) at least one hair-treatment composition of the instant disclosure; and (B) at least one conditioning composition, the conditioning composition comprising:
- at least 0.5 wt. % of at least one non-polymeric mono, di, or tricarboxylic acid, and/or a salt thereof; and
- one or more cationic surfactants; and
- one or more fatty compounds;
- wherein the at least hair-treatment composition of (A) and the at least one conditioning composition of (B) are separately contained.

The non-polymeric mono, di, or tricarboxylic acids, and/or salts thereof in the conditioning composition are those described throughout the disclosure. Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-91, Quaternium-18 hectorite, dimethylaminoethylchloride hydrochloride, cysteine hydrochloride, stearamidopropyl dimethylamine, behentrimonium methosulfate, cetrimonium methosulfate, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, stearalkonium bentonite, stearalkoniumhectonite, stearyl trihydroxyethyl propylenediamine dihydrofluoride, tallowtrimonium chloride, and hexadecyltrimethyl ammonium bromide. In some cases, the one or more cationic surfactants are selected from the group consisting of cetrimonium chloride, Quaternium-91, stearamidopropyl dimethylamine, behentrimonium methosulfate, cetrimonium methosulfate, and a mixture thereof.

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, and a mixture thereof. Further, the fatty compound(s) may be cetearyl alcohol and/or mineral oil.

The hair-treatment compositions may be packaged in a variety of different containers, such as, for example, a ready-to-use container. Non-limiting examples of useful packaging include tubes, jars, caps, unit dose packages, and bottles, including squeezable tubes and bottles.

Methods of treating hair according to the disclosure may vary but typically include applying a hair-treatment composition of the instant disclosure to the hair (wet, damp, or dry hair), allowing the hair-treatment to remain on the hair for a sufficient amount of time, and rinsing the hair-treatment composition from the hair. The hair-treatment composition may be applied to the hair before, during, or after other hair-treatment compositions (e.g., a chemical relaxer composition, a shampoo, a conditioner, a lotion, a gel, etc.).

As mentioned previously, the hair-treatment compositions are particularly useful for treating chemically treated hair, for example, hair that has been chemically treated with a lanthionizing agent. In some cases, a hair-treatment composition is applied to the hair shortly after a chemical treatment composition is rinsed from the hair (e.g., within about 5, 10, 15, 20, or 30 minutes from when the chemical treatment composition is rinsed from the hair), while the hair is still wet or damp. The hair-treatment composition may be allowed to remain on the hair for a period of time, for example from about a few seconds (1, 3, 5, or 10 seconds) to about 10, 20, or 30 minutes, or longer. In some cases the hair-treatment composition is applied to the chemically treated hair shortly after a chemical treatment composition is rinsed from the hair; and after applying the hair-treatment composition, the hair is subsequently treated with a shampoo and/or a conditioner, or a conditioning shampoo (all-in-one shampoo/conditioner). The hair-treatment composition may be rinsed from the hair prior to application of a shampoo and/or a conditioner, or a conditioning shampoo, or it may be allowed to remain on the hair during shampooing and/or conditioning and rinsed from the hair with the shampoo or the conditioner, or with the conditioning shampoo. For example, the hair-treatment composition may be applied to the hair and without rinsing the hair-treatment from the hair, a shampoo (or conditioner or conditioning shampoo) is subsequently applied to the hair (layered onto the hair-treatment composition already applied to the hair). Both compositions (the hair-treatment composition and the shampoo, conditioner, or conditioning shampoo) are rinsed from the hair together.

Moreover, the hair-treatment composition may be combined with a shampoo and/or a conditioner, or with a conditioning shampoo, prior to application to the hair. Combining the hair-treatment compositions with one or more additional hair treatment compositions (e.g., a shampoo, a conditioner, a conditioning shampoo, a rinse, etc.). For instance, the hair-treatment composition may be mixed with a shampoo (or conditioner or conditioning shampoo) prior to application to the hair. In this case, the mixture of the shampoo (or conditioner or conditioning shampoo) and the hair-treatment composition are simultaneously applied to the hair during the cleansing and/or conditioning process and simultaneously rinsed from the hair. Alternatively, the hair-treatment composition may be layered on top of (or lathered into) hair to which a shampoo (or conditioner or conditioning shampoo) has already been applied or vice versa. In this case, the hair-treatment composition may be applied to the hair first and without rinsing it from the hair, a shampoo (or conditioner or conditioning shampoo) is then subsequently applied to the hair. Alternatively, the shampoo (or conditioner or conditioning shampoo) may be first applied to the hair and without rinsing the shampoo (or conditioner or conditioning shampoo) from the hair, the hair-treatment composition is also applied to the hair. Then, the compositions are simultaneously rinsed from the hair.

Described above is the individual application of a hair-treatment composition or the combined or layered application of a hair-treatment composition with another composition (e.g., a shampoo, conditioner, conditioning shampoo, etc.). In some cases, a hair-treatment composition is individually applied to the hair and also combined or layered with another composition (e.g., a shampoo, conditioner, conditioning shampoo, etc.) that is also applied to the hair. For example, a hair-treatment composition may be applied to the hair. Subsequently, with or without rinsing the hair-treatment composition from the hair, another composition (e.g., a shampoo, conditioner, conditioning shampoo, etc.) in which the hair-treatment composition has been mixed may be applied to the hair.

When combined with another composition (e.g., a shampoo, conditioner, conditioning shampoo, etc.), the hair-treatment composition may be mixed with or used with in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair-treatment composition of the instant disclosure: another composition).

The hair-treatment compositions may be allowed to remain on the hair for a minimum amount of time before being rinsed from the hair, but allowing the hair-treatment composition to remain on the hair for an extended period of time is not needed. Conveniently, the hair-treatment compositions can be applied and allowed to remain on the hair for a period of time that is typical for regular shampooing and/or conditioning. For example, the hair-treatment composition (whether combined with another hair-treatment composition such as a shampoo or conditioner) may be applied to the hair and allowed to remain on the hair for a few seconds (1, 2, 3, 5, or 10 seconds) up to about 1, 2, 5, 10, 20, or 30 minutes, or longer.

When the hair-treatment composition is not applied to the hair, simultaneously with another composition (e.g., a shampoo, conditioner, conditioning shampoo, etc.), the hair-treatment composition may be applied to the hair immediately after or before the hair is treated with another composition (e.g., a shampoo, conditioner, conditioning shampoo, etc.). For example, the hair-treatment compositions may be applied to the hair within about 1, 2, 5, 10, or 20 minutes before or after another composition is applied to the hair.

Finally, as mentioned previously, the hair-treatment compositions are unique in their ability to strengthen hair and improve smoothness, softness, and suppleness. Accordingly, the instant disclosure relates to methods for strengthening hair and for imparting smoothness, softness, and suppleness.

More exhaustive but non-limiting lists of components useful in the hair-treatment compositions disclosed herein are provided below.
Amines
  Diamines
    Non-limiting examples of diamines that may be useful may be primary amines and secondary amines. The diamine can include both primary and secondary amine groups. Optional diamines may include at least one ethylene oxide group. For example, between 1 and 4 ethylene oxide groups can be present in the diamine. The diamine may optionally include propylene oxide groups. For example, between 1 and 4 propylene oxide groups can be present in the diamine. Non-limiting examples of diamines include 4,9-dioxadodecane-diamine; 4, 7, 10-trioxa-1,13-tridecanediamine; ethylenediamino; polyoxypropylene diamine; polyethylene glycol diamine; triethylene glycol diamine (2OE); n-(2-hydroxyethyl)-ethylenediamine; 1,3-diaminopropane; 1,7-diaminoheptane; 1,4-diaminobutane; 1,2-diaminopropane; 1,6-diaminohexane; 1,11-diamino-3,6,9-trioxaundecane; 1,5-diaminopentane; polyoxyethylene diamine; 2,2-dimethyl-1,3-propanediamine; 2,2-bis(aminoethoxy)propane; 4,7,10-trioxa-1,13-tridecanediamine; 1,3-diaminopentane; 4,7,10-trioxa-1,13; 1,5-diamino-2-methylpentane; (3s,4s)-(−)-3,4-hexanediamine dihydrochloride; 1,9-diaminononane, and mixtures thereof.

In some cases, diamines may be selected from the group consisting of 4,9-dioxadodecane-diamine, 4, 7, 10-trioxa-1,13-tridecanediamine, ethylenediamino, polyoxypropylene diamine, polyethylene glycol diamine, triethylene glycol diamine (2OE); n-(2-hydroxyethyl)-ethylenediamine; 1,3-diaminopropane, 1,7-diaminoheptane, 1,4-diaminobutane, 1,2-diaminopropane, 1,6-diaminohexane, 1,11-diamino-3,6,9-trioxaundecane, 1,5-diaminopentane, polyoxyethylene diamine, 2,2-dimethyl-1,3-propanediamine, 2,2-bis(aminoethoxy)propane, 4,7,10-trioxa-1,13-tridecanediamine, 1,3-diaminopentane, 4,7,10-trioxa-1,13; 1,5-diamino-2-methylpentane, (3s,4s)-(−)-3,4-hexanediamine dihydrochloride, 1,9-diaminononane, and mixtures thereof.

Polyamines

Polyamines have more than two amino groups. In some cases, the composition of the instant disclosure may include one or more polyamines, but in some cases, the compositions are free or essentially free of polyamines. The polyamine may be, for example, aminated polysaccharides comprising multiple amino groups, such as, for example, hydrolysates of aminated polysaccharides.

The polyamine may also be a polymer comprising multiple amino groups including homopolymers, copolymers, and terpolymers.

In some cases, polyamines are chosen from polyethyleneimines. Polyethyleneimines may optionally be substituted. Non-limiting examples of polyethyleneimines which may be used include LUPASOL products commercially available from BASF. Suitable examples of LUPASOL polyethyleneimines include LUPASOL PS, LUPASOL PL, LUPASOL PR8515, LUPASOL G20, LUPASOL G35 as well as LUPASOL SC Polythyleneimine Reaction Products (such as LUPASOL SC-61B, LUPASOL SC-62J, and LUPASOL SC-86X). Other non-limiting examples of polyethyleneimines which may be used in the composition according to the present invention are the EPOMIN products commercially available from Aceto. Suitable examples of EPOMIN polyethyleneimines include EPOMIN SP-006, EPOMIN SP-012, EPOMIN SP-018, and EPOMIN P-1000. Suitable polyamines s also be chosen from polyvinylamines. Examples thereof include LUPAMINES 9095, 9030, 9010, 5095, 1595 from BASF.

The polyamine compounds can also be substituted. An example of such a compound is PEG-15 Cocopolyamine from Cognis.

In some cases, the polyamine is chosen from proteins and protein derivatives. Non-limiting examples of suitable proteins and protein derivatives f include those listed at pages 1701 to 1703 of the C.T.F.A. International Cosmetic Ingredient Dictionary and Handbook, $8^{th}$ edition, vol. 2, (2000), which is incorporated herein by reference in its entirety. In some cases, the at least one polyamine is chosen from wheat protein, soy protein, oat protein, collagen, and keratin protein.

The polyamine may be an alkoxylated polyamine. The alkoxylated polyamines may be chosen from amine compounds having at least two amino groups and at least one degree of alkoxylation. The alkoxylation is provided by an alkylene oxide group which may be chosen from ethylene oxide and propylene oxide. Non-limiting examples of suitable alkoxylated polyamines include compounds corresponding to the following formula:

wherein R represents a —CH2-, —CH$_2$CH$_2$—, —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted; x, y, and z independently of one another, represent numbers of from 0 to about 100; R' represents hydrogen, or an alkyl group, preferably a methyl group; and The sum of x+y+z is at least 1. In some cases, R is a linear or branched, acyclic alkyl or alkenyl group or an alkyl phenyl group; x, y, and z independently of one another, preferably represent numbers ranging from 2 to 100.

Non-limiting examples of the alkoxylated polyamines include, for example, tetradecyloxypropyl-1,3-diaminopropane; a $C_{12-14}$ alkyl oxypropyl-1,3-diaminopropane; a $C_{12-15}$ alkyloxypropyl amine and other similar materials that are commercially available from Tomah under the tradename of TOMAH DA-17. Other examples of alkoxylated polyamines are diamine compounds belonging to the Jeffamine series such as the JEFFAMINE D and JEFFAMINE ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. JEFFAMINE D series compounds are amine terminated PPGs (polypropylene glycols) and JEFFAMINE ED series compounds are polyether diamine based with a predominantly PEG (polyethylene glycol) backbone.

Other non-limiting examples of suitable alkoxylated polyamines in the diamine form include compounds corresponding to the following formula:

wherein x is 2 or 3.

Examples of alkoxylated polyamines are diamine compounds belonging to the JEFFAMINE series available from Huntsman Corporation, Salt Lake City, Utah, such as JEFFAMINE EDR148, and JEFFAMINE EDR176.

Additional non-limiting examples of alkoxylated polyamines in the triamine form include compounds corresponding to the following formula:

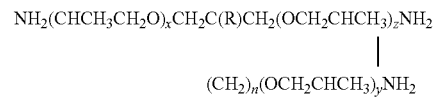

wherein R is hydrogen, —CH$_2$ or —C$_2$H$_5$, n=0 or 1, and x, y, and z independently of one another, represent numbers of from 0 to 100 and the sum of x+y+z is at least 1.

Examples of alkoxylated polyamines are triamine compounds belonging to the JEFFAMINE series such as the JEFFAMINE T series available from Huntsman Corporation, Salt Lake City, Utah. Examples of the JEFFAMINE T series compounds are JEFFAMINE T403, JEFFAMINE T3000, and JEFFAMINE T5000. JEFFAMINE T series compounds are triamines made by reacting PO with a triol initiator followed by aminating the terminal hydroxyl groups.

Alkylamines and Alkanolamines

The one or more alkylamines and/or one or more alkanolamines that may be included in the compositions include compounds of formula (II):

NR$_3$R$_4$R$_5$          (II)

wherein R$_3$, R$_4$ and R$_5$ are independently H, C$_1$-C$_{40}$ alkyl, C$_1$-C$_{40}$ monohydroxyalkyl or C$_2$-C$_{40}$ polyhydroxyalkyl, provided that at least one of R$_3$, R$_4$ and R$_5$ is an alkyl or mono or polyhydroxyalkyl. In some cases, R$_3$, R$_4$ and R$_5$ are independently H, C$_1$-C$_2$ alkyl, C$_1$-C$_{20}$ monohydroxyalkyl or C$_2$-C$_{20}$ polyhydroxyalkyl, provided that at least one of R$_3$, R$_4$ and R$_5$ is an alkyl or mono or polyhydroxyalkyl. Finally, R$_3$, R$_4$ and R$_5$ may independently be H, C$_1$-C$_{10}$ alkyl, C$_1$-C$_{10}$ monohydroxyalkyl or C$_2$-C$_{10}$ polyhydroxyalkyl, provided that at least one of R$_3$, R$_4$ and R$_5$ is an alkyl or mono or polyhydroxyalkyl.

Non-limiting examples of alkanolamines include monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

Further non-limiting examples of alkylamines include aliphatic amine compounds corresponding to the following formula and their salts:

RN(R')$_2$ wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. In some cases, the groups R', which may be identical or different, are H or a methyl group.

In some cases, alkylamines include, but are not limited to the following examples: dimethyl lauramine, dimethyl behenamine, dimethyl cocamine, dimethyl myristamine, dimethyl palmitamine, dimethyl stearamine, dimethyl tallowamine, dimethyl soyamine, stearamine, soyamine, cocamine, lauramine, palmitamine, oleamine, tallow amine and mixtures thereof.

Other non-limiting examples of alkyl monoamines include amidoamine compounds corresponding to the following formula and their salts:

RCONHR'N(R")$_2$ wherein: R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R" is H or a hydrocarbon radical containing less than 6 carbon atoms. In addition, R" is linear or branched, acyclic or cyclic, saturated or unsaturated, substituted or unsubstituted. Typically, R" is a linear or branched, acyclic alkyl or alkenyl group. In some cases, R" is H or a methyl group.

Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

Additional Amines

Additional amines that may be useful include alkoxylated monoamines. The alkoxylated monoamines are compounds having an amino group and at least one degree of alkoxylation. The alkoxylation is provided by an alkylene oxide group which is often chosen from ethylene oxide and propylene oxide.

Non-limiting examples of suitable alkoxylated monoamines include compounds corresponding to the following formula:

RN[(R'CHCH$_2$O)$_x$H][(R'CHCH$_2$O)$_y$H]

wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 provided that the sum of x+y is >0; the groups R', which may be identical or different, represent hydrogen, or an alkyl group such as a methyl group. Typically, R is a linear or branched, acyclic alkyl or alkenyl group or an alkyl phenyl group; x and y, independently of one another, are each typically a number from 0 to 30. Typically, one R' group is hydrogen, and the other one is methyl.

Non-limiting examples of alkoxylated monoamines include PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding the following formula:

RNR"[(R'CHCH$_2$O)$_x$H]

wherein R is a hydrocarbon radical containing at least 6 carbon atoms. R can be linear or branched, acyclic or cyclic, saturated or unsaturated, aliphatic or aromatic, substituted or unsubstituted; x represents a number of from 1 to 100; R' represents hydrogen, or an alkyl group such as in particular a methyl group; and R" is a hydrogen or a hydrocarbon radical. Typically, R is a linear or branched, acyclic alkyl or alkenyl group or an alkyl phenyl group; x is typically a number from 1 to 30. When R" is a hydrocarbon radical group, this group may be linear or branched, saturated or unsaturated, substituted or unsubstituted. The hydrocarbon radical represented by R" may also contain an alkoxylated moiety (as defined by [(R'CHCH$_2$O)$_y$H]), and/or heteroatoms such as nitrogen. When R" contains at least one alkoxylated moiety, the total number of alkoxylation in the formula may range from 1 to 120. Examples of alkoxylated monoamines include PEG-3 Tallow Aminopropylamine, PEG-10 Tallow Aminopropylamine, PEG-15 Tallow Aminopropylamine, and PEG-105 Behenyl Propylenediamine.

Additional non-limiting examples of alkoxylated monoamines include compounds corresponding to the following formula:

R(R'CHCH$_2$O)$_x$(R'CHCH$_2$O)$_y$NH$_y'$ wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 with the proviso that the sum of x+y is >0; the groups R', which may be identical or different, represent hydrogen, or an alkyl group such as in particular a methyl group. Typically, R is a linear or branched, acyclic alkyl or alkenyl group or an alkyl phenyl group; x and y, independently of one another, are each typically a number from 0 to 30. Examples of alkoxylated monoamines include polyetheramines containing a monoamine group. These polyetheramines are commercially available from Hunstman under the tradename JEFFAMINE (M series such as M-600, M-1000, M-2005 and M-2070) and SURFONAMINE series (B-60, B-100, B-200, L-100, L-200, L-207, L-300).

Alkoxysilanes

The one or more alkoxysilanes often include at least one solubilizing functional group. As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents. Suitable solubilizing functional groups include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

In some cases, the one or more alkoxysilanes comprising at least one solubilizing functional group may comprise two or three alkoxy groups. For example, the alkoxy functional groups may be chosen from methoxy and ethoxy functional groups.

In some cases, the one or more alkoxysilanes comprising at least one solubilizing functional group may be selected from compounds of the following formula:

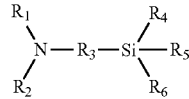

wherein, R$_4$ is chosen from halogen atoms, OR' groups, and R$_{11}$ groups;
R$_5$ is chosen from halogen atoms, OR" groups, and R$_{12}$ groups;
R$_6$ is chosen from halogen atoms, OR'" groups, and R$_{13}$ groups;
R$_1$, R$_2$, R$_3$, R', R", R'", R$_{11}$, R$_{12}$, and R$_{13}$, which may be identical or different, are chosen from linear and branched, saturated and unsaturated hydrocarbon groups, optionally bearing at least one additional chemical group, wherein R$_1$, R$_2$, R', R", and R'" may also be chosen from hydrogen; provided that at least two groups R$_4$, R$_5$, and R$_6$ are different from R$_{11}$, R$_{12}$, and R$_{13}$, and at least two groups R', R", and R'" are not hydrogen.

The one or more alkoxysilanes comprising at least one solubilizing functional group may also be one or more compounds chosen from compounds of the following formula:

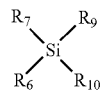

wherein R$_9$ is chosen from halogen atoms and OR'$_9$ groups;
R$_{10}$ is chosen from halogen atoms and OR'$_{10}$ groups;
R'$_9$ and R'$_{10}$, which may be identical or different, are chosen from hydrogen, and linear and branched, saturated and unsaturated C$_1$-C$_{14}$ hydrocarbon groups
R$_7$ is a non hydrolyzable functional group providing a cosmetic effect; and
R$_8$ is a non hydrolyzable functional group bearing at least one function chosen from amines, carboxylic acids and salts thereof, sulfonic acids and salts thereof, polyols such as glycol, polyethers such as polyalkylene ether, and phosphoric acids and salts thereof; and provided that at least one of R$_9$ and R$_{10}$ is not a halogen.

In some cases, the one or more alkoxysilanes comprising at least one solubilizing functional group may be chosen from compounds of the following formula:

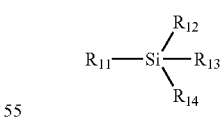

wherein R$_{12}$ is chosen from halogen atoms, OR'$_{12}$ groups, and R$_O$ groups;
R$_{13}$ is chosen from halogen atoms, OR'$_{13}$ groups, and R'$_O$ groups;
R$_{14}$ is chosen from halogen atoms, OR'$_{14}$ groups, and R"$_O$ groups;
R$_{11}$ is chosen from groups bearing at least one function chosen from carboxylic acids and salts thereof, sulfonic acids and salts thereof, and polyalkylethers;
R$_O$, R'$_O$, R"$_O$, R'$_{12}$, R'$_{13}$, and R'$_{14}$, which may be identical or different, are chosen from linear and branched, saturated and unsaturated, C1-$C_{14}$ hydrocarbon groups optionally bearing at least one additional chemical functional group chosen from carboxylic acids and salts thereof, sulfonic acids and salts thereof, and polyalkylether functions, and wherein $R'_{12}$, $R'_{13}$, and $R_{14}$ may also be chosen from hydrogen; provided that at least two groups from $R_{12}$, $R_{13}$ and $R_{14}$ are different from $R_O$, $R'_O$, and $R''_O$ groups; and provided further that at least two of the groups $R'_{12}$, $R'_{13}$, and $R'_{14}$ are not hydrogen.

According to another embodiment, the one or more alkoxysilanes comprising at least one solubilizing functional group may be chosen from compounds of the following formula:

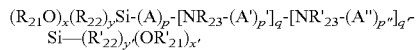

wherein $R_{21}$, $R_{22}$, $R'_{21}$, and $R'_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x is an integer ranging from 1 to 3;
y is 3-x;
x' is an integer ranging from 1 to 3;
y' is 3-x',
p, p', p'', q, and q' can each be 0 or 1, wherein at least one of q or q' is not equal to zero;
A, A', and A'', which may be identical or different, are chosen from linear and branched $C_1$-$C_{20}$ alkylene divalent radicals; and $R_{23}$ and $R'_{23}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

The one or more alkoxysilanes comprising at least one solubilizing functional group may also be chosen from compounds of the following formula:

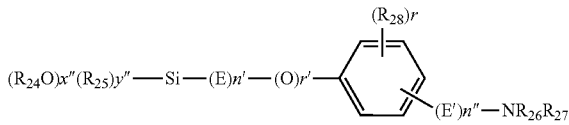

wherein $R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x'' is 2 or 3; [0170] y'' is 3-x'';
n' is 0 or 1;
n'' is 0 or 1;
E and E', which may be identical or different, are chosen from linear and branched $C_1$-$C_{20}$ alkylene divalent radicals;
$R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_1$-$C_{20}$ alcohol ester, amine, amide, carboxyl, alkoxysilane, hydroxyl, carbonyl, and acyl groups;

r is an integer ranging from 0 to 4;
r'=0 or 1; and
$R_{28}$ is chosen from hydrogen and linear and branched, saturated and unsaturated hydrocarbon chains, comprising, optionally at least one heteroatom, optionally interrupted by or substituted with at least one entity chosen from ether, alkyl alcohol ester, amine, carboxyl, alkoxysilane, alkyl aryl, hydroxyl, and carbonyl groups, and aromatic, heterocyclic, and non-heterocyclic rings.

According to a further exemplary embodiment, one or more alkoxysilanes comprising at least one solubilizing functional group may be chosen from compounds of the following formula:

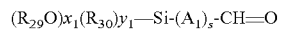

wherein $R_{29}$ and $R_{30}$, independently, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

$x_1$ is 2 or 3;
$y_1$ is 3-$x_1$;
$A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_6$-$C_{30}$ aryl, hydroxyl, and carbonyl groups; and
s is 0 or 1.

In some instances, one or more alkoxysilanes comprising at least one solubilizing functional group is chosen from compounds of the following formula:

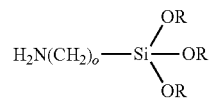

wherein the R radicals, which may be identical or different, are chosen from $C_1$-$C_6$ alkyl radicals and n is an integer ranging from 1 to 6, for example, from 2 to 4.

The alkoxysilanes useful in the present disclosure can be chosen from alkoxysilanes comprising a silicon atom in a formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Exemplary alkoxysilanes include, but are not limited to, 3-mercaptopropyltriethoxysilane and aminoalkyltrialkoxysilanes such as 3-aminopropyltriethoxysilane, as described in French Patent Application No. FR2789896, incorporated by reference herein. Other useful alkoxysilanes are cited, for example, in EP1216022, incorporated by reference herein, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST. In some cases, the alkoxysilanes may comprise at least one hydrocarbon chain containing fluorine atoms. Non-limiting examples include but are not limited to the 3,3,3-trifluoropropyltriethoxysilane or tridecafluorooctyltriethoxysilane compounds described in EP1510197, incorporated by reference herein.

It is also contemplated that these alkoxysilanes may carry a solubilizing, non-hydrolysable group such as amino groups, carboxylic acids, sulphonic acids, sulphates, quaternary ammoniums, polyalcohols, polyether and phosphates. One possible example of the foregoing types of alkoxysilanes is aminopropyl-N-(4,2-dinitrophenyl)aminopropyldiethoxysilane. Additional exemplary compounds of this type are described, for example, in EP1216023, which is herein incorporated by reference. Non-limiting examples of useful alkoxysilanes include 3-mercaptopropyltriethoxysilane and aminoalkyltrialkoxysilanes such as 3-aminopropyltriethoxysilane ("APTES", described in French Patent Application No. FR 2 789 896, incorporated herein by reference), and mixtures thereof. In some cases, the hair-treatment compositions include 3-aminopropyltriethoxysilane.

Cationic Polymers

Non-limiting examples of cationic polymers include poly(methacryloyloxyethyl trimethylammonium chloride), polyquaternium-37, quaternized cellulose derivatives, polyquaternium-4, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some instances, the one or more cationic polymers may be selected from the group consisting of polyquaternium-4, polyquaternium-10, cationic guar derivatives, and a mixture thereof.

The cationic polymers can be a monoalkyl quaternary amine, such as stearyltrimonium chloride, soyatrimonium chloride or coco-ethyldimonium ethosulfate. Other suitable cationic polymers include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic polymers may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic polymers are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic polymers are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 is sold under the trademark MERQUAT-100, and is described as having a weight average molecular weight of approximately 100,000. A copolymer reaction product of dimethyldiallylammonium chloride with acrylamide monomers is named Polyquaternium-7 is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10. Also useful are quaternized copolymers of hydroxyethylcellulose and dimethyldimethylammonium chloride, having the name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

Implementation of the present disclosure is provided by way of the following examples. The examples serve to illustrate the technology without being limiting in nature.

Example 1

(Hair-Treatment Compositions)

|  |  | Comparative | | | Inventive |
| --- | --- | --- | --- | --- | --- |
|  | INCI US | #1 | #2 | #3 | #4 |
| Dicarboxylic Acid | MALONIC ACID | 9.6 | 9.6 | 9.6 | 9.6 |
| Alkanolamine | MONO-ETHANOLAMINE | 4.1 | 3.5 | 4.1 | 3.5 |
| Alkoxysilane | AMINOPROPYL TRIETHOXYSILANE | — | 2.5 | — | 2.5 |
| Cationic Polymer | POLY QUATERNIUM-6 | — | — | 0.4 | 0.4 |
| Dye(s) | OPTIONAL COMPONENT | 0-3 | 0-3 | 0-3 | 0-3 |
| Fragrance(s) | OPTIONAL COMPONENT | 0-3 | 0-3 | 0-3 | 0-3 |
| Water | WATER | Q.S. | Q.S. | Q.S. | Q.S. |

Example 2

Attributes

Testing was carried out to determine the influence of the hair-treatment compositions of Example 1 (Formulations #1, #2, #3, and #4) on chemically relaxed hair. The chemical relaxer composition and the conditioner used in the testing are shown in the tables below.

Chemical Relaxer Composition

|  | INCI US Name | #5 wt. % |
| --- | --- | --- |
| Active | SODIUM HYDROXIDE (100%) | 2.1 |
| Fatty Compounds | PETROLEUM JELLY, COCOA BUTTER, MINERAL OIL, AND/OR SHEA BUTTER | 36 |
| Surfactants | PEG-75 LANOLIN, CETEARYL ALCOHOL, BEHENTRIMONIUM METHOSULFATE, AND/OR POLYSORBATE 60 | 12.8 |
| Cationic Polymer | POLYQUATERNIUM-6 | 0.5 |
| Solvent | PROPYLENE GLYCOL | 3 |
| Fragrance | OPTIONAL COMPONENT | 0-2 |
| Water | WATER | Q.S |

Conditioner

|  | INCI US | #6 |
| --- | --- | --- |
| Active | MALONIC ACID | 1.7 |
| Cationic Surfactant(s) | QUATERNIUM-91, CETRIMONIUM CHLORIDE, STEARAMIDOPROPYL DIMETHYLAMINE, BEHENTRIMONIUM METHOSULFATE, AND/OR CETRIMONIUM METHOSULFATE | 1.9 |
| Fatty Compound(s) | CETEARYL ALCOHOL AND/OR MINERAL OIL | 4.3 |
| Cationic Polymer | POLYQUATERNIUM-37 | 0.2 |
| Water-Soluble Solvent(s) | GLYCERIN AND/OR PROPYLENE GLYCOL | 3.5 |
| Thickener(s) | OPTIONAL COMPONENT | 0-2 |
| Preservative(s) | OPTIONAL COMPONENT | 0-2 |
| Fragrance(s) | OPTIONAL COMPONENT | 0-2 |
| Water | WATER | Q.S. |

Hair swatches were treated with either only the chemical relaxer composition of Formulation #5 or with the chemical relaxer composition of Formulation #5 followed by treatment with one of the hair-treatment compositions of Example 1 (Formulation #1, #2, #3, or #4) and the conditioner of Formulation #6.

The hair swatches treated with only the chemical relaxer composition of formulation #5 were rinsed, shampooed, and evaluated by experts.

The hair swatches treated with the chemical relaxer composition of Formulation 5, a hair-treatment composition of Example 1, and the conditioner of Formulation #6 were treated as follows. After the chemical relaxer composition of Formulation #5 was rinsed from the hair, one of the hair-treatment compositions of Example 1 (Formulation #1, #2, #3, or #4) was applied to the hair (while the hair was still wet from rinsing the chemical relaxer composition from the hair). The hair-treatment composition of Example 1 were allowed to remain on the hair for about 10 minutes. After about 10 minutes, without rinsing the hair-treatment compositions from the hair, the conditioner of Formulation #6 was applied to the hair (the conditioner was layered onto the hair that was already covered with the hair-treatment composition). The conditioner was then allowed to remain on the hair for about 10 minutes. After allowing the conditioner to remain on the hair for about 10 minutes, the conditioner and the underlying hair-treatment composition were rinsed from the hair. The hair was shampooed, blow dried, and evaluated by a panel of experts. The results of the expert evaluations are summarized in the table below, where "✓" represents the baseline for each attribute for the hair swatches treated with only the chemical relaxer composition. "✓✓" represents an appreciable improvement in the attribute; and "✓✓✓" represents an even better, significant improvement in the attribute.

|  | Relaxer Alone | Relaxer Example 1 Conditioner | Relaxer Example 2 Conditioner | Relaxer Example 3 Conditioner | Relaxer Example 4 Conditioner |
|---|---|---|---|---|---|
| Softness | = | ✓ | ✓ | ✓✓ | ✓✓✓ |
| Smoothness | = | ✓ | ✓ | ✓✓ | ✓✓✓ |
| Thick Feeling | = | = | ✓ | = | ✓✓ |

The results show that a significant improvement with respect to softness and smoothness is achieved and an appreciable improvement with respect to thick feeling is achieved when chemically relaxed hair is treated with the hair-treatment composition of formulation #4 of Example 1. The hair-treatment composition of Formulation #4 of Example 1 includes: at least 0.5 wt. % of at least one non-polymeric mono, di, or tricarboxylic acid (malonic acid); an amine (monethanolamine); a cationic silane (aminopropyltriethoxysilane); and a cationic polymer (polyquaternium-6). The data show that if any one of these four components is omitted, one or more of the cosmetic attributes suffer.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts, for example, the salts of the amino acids, the amino sulfonic acids, and the non-polymeric mono, di, and/or tricarboxylic acids, which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

Some of the various categories of components identified for the various composition described herein, including the hair-treatment compositions, may overlap. In such cases where overlap may exist between two or more components, a single overlapping compound does not represent more than one component. For example, a homopolymer of methyl quaternized dimethylaminoethyl methacrylate may be characterized as both a cationic polymer component and a thickening agent component. If a particular composition is described as including both a cationic polymer and a thickening agent, a single homopolymer of methyl quaternized dimethylaminoethyl methacrylate would serve as only the cationic polymer or only the thickening agent (the compound does not serve as both the cationic polymer and the thickening agent in the same composition).

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat," and its grammatical variations, relates to contacting hair with the hair-treatment compositions of the present disclosure.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair-treatment composition comprising: at least 0.5 to about 20 wt. % of malonic acid and/or a salt thereof; about 1 to about 20 wt. % of monoethanolamine; about 0.1 to about 20 wt. % of 3-mercaptopropyltriethoxysilane and/or 3-aminopropyltriethoxysilane; and about 0.01 to about 10 wt. % of one or more cationic polymers, wherein all percentages by weight are based on the total weight of the hair-treatment composition.

2. A hair-treatment composition of claim 1, wherein the one or more cationic polymers are selected from the group consisting of poly(methacryloyloxyethyl trimethylammonium chloride), polyquaternium-37, quaternized cellulose derivatives, polyquaternium-4, polyquaternium-6, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof.

3. A hair-treatment composition of claim 1, wherein the one or more cationic polymers comprises a polyquaternium.

4. A hair-treatment composition of claim 1, wherein the one or more cationic polymers comprises polyquaternium-6.

5. A kit comprising:
(A) at least one hair-treatment composition of claim 1; and
(B) at least one additional hair-treatment composition that is different than the hair-treatment composition of (A); wherein the at least hair-treatment composition of (A) and the at least one additional hair-treatment composition of (B) are separately contained.

6. A kit of claim 5, wherein the at least one additional hair-treatment composition is a chemical relaxer composition, an oxidative hair dye, a shampoo, a conditioner, a bleach, or a direct dye.

7. A kit of claim 5, wherein the at least one additional hair-treatment composition is a conditioner.

8. A kit of claim 5, wherein the at least one additional hair-treatment composition is a chemical relaxer composition.

9. A kit of claim 5 comprising at least two additional hair-treatment compositions of (B), wherein at least one of the additional hair-treatment compositions is a chemical relaxer composition and at least one or the additional hair-treatment compositions is a conditioner.

10. A kit comprising:
(A) at least one hair-treatment composition of claim 1; and
(B) at least one conditioning composition, the conditioning composition comprising:
at least 0.5 wt. % of at least one non-polymeric mono, di, or tricarboxylic acid, and/or a salt thereof; and
one or more cationic surfactants; and
one or more fatty compounds;
wherein the at least hair-treatment composition of (A) and the at least one conditioning composition of (B) are separately contained.

11. A method for treating hair comprising applying the hair-treatment composition of claim 1 to the hair.

* * * * *